United States Patent
Schlapfer et al.

(10) Patent No.: US 6,585,740 B2
(45) Date of Patent: Jul. 1, 2003

(54) BONE SCREW

(75) Inventors: Fridolin J. Schlapfer, Glarus (CH); Martin Hess, Holstein (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/864,449

(22) Filed: May 25, 2001

(65) Prior Publication Data

US 2002/0016594 A1 Feb. 7, 2002

Related U.S. Application Data

(63) Continuation of application No. PCT/CH98/00504, filed on Nov. 26, 1998.

(51) Int. Cl.$^7$ ............................................. A61B 17/56
(52) U.S. Cl. ........................ 606/73; 411/380; 411/401
(58) Field of Search ............................. 606/65, 72, 73, 606/61; 411/380, 383, 386, 393, 394, 411, 412, 426, 401, 381, 379, 382; 623/23.27

(56) References Cited

U.S. PATENT DOCUMENTS

| | | | | |
|---|---|---|---|---|
| 422,307 A | * | 2/1890 | Libbey | .................. 411/412 |
| 1,135,516 A | | 4/1915 | Frauenheim | |
| 1,926,925 A | | 9/1933 | Wescott | |
| 2,060,593 A | | 11/1936 | Schaurte et al. | |
| 2,123,764 A | | 7/1938 | Berry | |
| 2,267,925 A | | 12/1941 | Johnston | |
| 2,382,019 A | | 8/1945 | Miller | |
| 2,570,465 A | | 10/1951 | Lundholm | |
| 2,859,983 A | * | 11/1958 | May | .................. 285/90 |
| 2,871,752 A | | 2/1959 | Stern | |
| 3,051,169 A | | 8/1962 | Grath | |
| 3,256,661 A | | 6/1966 | Fischer | |
| 3,374,016 A | * | 3/1968 | Melton et al. | ............... 403/125 |
| 3,499,222 A | | 3/1970 | Linkow et al. | |

(List continued on next page.)

FOREIGN PATENT DOCUMENTS

| | | |
|---|---|---|
| CA | 1 162 124 | 2/1984 |
| DE | 603 330 | 9/1934 |
| DE | 195 29 901 A1 | 2/1996 |
| EP | 0 276 153 | 7/1988 |
| EP | 0 451 932 A1 | 10/1991 |
| EP | 0 491 211 A1 | 11/1991 |
| EP | 0 471 419 A2 | 2/1992 |
| EP | 0 657 142 A1 | 11/1994 |
| EP | 0 669 110 A2 | 2/1995 |
| EP | 0 574 517 B1 | 5/1995 |
| EP | 0 682 917 A1 | 11/1995 |
| EP | 0 695 537 A1 | 2/1996 |
| EP | 0 726 064 A2 | 8/1996 |
| EP | 0 941 705 A2 | 9/1999 |
| GB | 484654 | 5/1938 |
| JP | 08052156 | 2/1996 |
| JP | 08229051 | 9/1996 |
| JP | 09000539 | 1/1997 |
| JP | 10052439 | 2/1998 |
| JP | 10243953 | 7/1998 |
| JP | 0 856 293 A1 | 8/1998 |
| JP | 10277052 | 10/1998 |
| WO | WO 90/02526 | 3/1990 |
| WO | WO 91/09572 | 7/1991 |
| WO | WO 93/15682 | 8/1993 |

*Primary Examiner*—Eduardo C. Robert
(74) *Attorney, Agent, or Firm*—Pennie & Edmonds LLP

(57) ABSTRACT

The central portion of the screw according to the invention has a series of segments varying in diameter, typically having a segment located near the screw head with a large diameter, a segment located near the front portion with a small diameter, and intermediate segments tapering in the direction of the segment with the small diameter. A continuous thread extends along the central portion from the screw head to the screw tip where the thread has a substantially uniform outside diameter along the entire length of the central portion. The screw, which is particularly well-suited as a pedicle screw, has improved resistance to tearing, cutting and bending, and, largely independent of bone quality, good hold in bone.

34 Claims, 2 Drawing Sheets

U.S. PATENT DOCUMENTS

| | | |
|---|---|---|
| 3,541,918 A | 11/1970 | Johnson |
| 3,682,507 A | 8/1972 | Waud |
| 3,867,932 A | 2/1975 | Huene |
| 4,016,874 A | 4/1977 | Maffei et al. |
| 4,175,555 A | 11/1979 | Herbert |
| 4,259,072 A | 3/1981 | Hirabayashi et al. |
| 4,463,753 A | 8/1984 | Gustilo |
| 4,537,185 A | 8/1985 | Stednitz |
| 4,576,534 A | 3/1986 | Barth et al. |
| 4,621,963 A | 11/1986 | Reinwall |
| 4,640,271 A | 2/1987 | Lower |
| 4,754,749 A | 7/1988 | Tsou |
| 4,790,850 A | 12/1988 | Dunn et al. |
| 4,861,206 A | 8/1989 | Riedel |
| 4,870,957 A | 10/1989 | Goble et al. |
| 4,877,364 A | 10/1989 | Sorrentino |
| 4,878,793 A | 11/1989 | Hewison |
| 4,927,421 A | 5/1990 | Goble et al. |
| 4,950,270 A | 8/1990 | Bowman et al. |
| RE33,348 E | 9/1990 | Lower |
| 4,959,938 A | 10/1990 | De Caro |
| 4,963,144 A | 10/1990 | Huene |
| 4,966,024 A | 10/1990 | Hewison |
| 5,019,079 A | 5/1991 | Ross |
| 5,100,405 A | 3/1992 | McLaren |
| 5,116,337 A | 5/1992 | Johnson |
| 5,120,171 A | 6/1992 | Lasner |
| 5,139,499 A | 8/1992 | Small et al. |
| 5,139,520 A | 8/1992 | Rosenberg |
| 5,151,104 A | 9/1992 | Kenna |
| 5,152,764 A | 10/1992 | Goble |
| 5,156,616 A | 10/1992 | Meadows et al. |
| 5,169,400 A | 12/1992 | Mühling et al. |
| 5,180,382 A | 1/1993 | Frigg et al. |
| 5,188,496 A | 2/1993 | Giannuzzi |
| 5,190,544 A | 3/1993 | Chapman et al. |
| 5,201,735 A | 4/1993 | Chapman et al. |
| 5,217,462 A | 6/1993 | Asnis et al. |
| 5,226,766 A | 7/1993 | Lasner |
| 5,259,398 A | 11/1993 | Vrespa |
| 5,300,076 A | 4/1994 | Leriche |
| 5,312,412 A | 5/1994 | Whipple |
| 5,324,199 A | 6/1994 | Branemark |
| 5,358,367 A | 10/1994 | Yang |
| 5,360,448 A | 11/1994 | Thramann |
| 5,362,236 A | 11/1994 | Branemark |
| 5,364,400 A | 11/1994 | Rego, Jr. et al. |
| 5,417,533 A | 5/1995 | Lasner |
| 5,433,570 A | 7/1995 | Köppel |
| 5,443,509 A | 8/1995 | Boucher et al. |
| 5,456,685 A | 10/1995 | Huebner |
| 5,492,442 A | 2/1996 | Lasner |
| 5,496,326 A | 3/1996 | Johnson |
| 5,536,127 A | 7/1996 | Pennig |
| 5,544,993 A | 8/1996 | Härle |
| 5,562,672 A | 10/1996 | Huebner et al. |
| 5,607,428 A | 3/1997 | Lin |
| 5,658,288 A | 8/1997 | Kim |
| 5,683,392 A * | 11/1997 | Richelsoph et al. ........ 606/61 |
| 5,733,286 A * | 3/1998 | Errico et al. ............... 606/61 |
| 5,735,898 A | 4/1998 | Brånemark |
| 5,743,908 A | 4/1998 | Kim |
| 5,842,865 A | 12/1998 | Bassett et al. |
| 5,863,167 A * | 1/1999 | Kaneko .................... 411/426 |
| 5,865,584 A | 2/1999 | Onofrio |
| 5,868,749 A | 2/1999 | Reed |
| 5,871,486 A | 2/1999 | Huebner et al. |
| 5,882,162 A | 3/1999 | Kaneko |
| 5,899,906 A | 5/1999 | Schenk |
| 5,925,048 A | 7/1999 | Ahmad et al. |
| 5,947,965 A | 9/1999 | Bryan |
| 5,968,047 A | 10/1999 | Reed |
| 6,001,101 A | 12/1999 | Augagneur et al. |
| 6,030,162 A | 2/2000 | Huebner |
| 6,059,785 A | 5/2000 | Schavan et al. |
| 6,306,138 B1 * | 10/2001 | Clark et al. ................ 606/65 |

* cited by examiner

BONE SCREW

CROSS-REFERENCE TO RELATED APPLICATIONS

This application is a continuation of the U.S. national stage designation of co-pending International Patent Application PCT/CH98/00504, filed Nov. 26, 1998, the entire content of which is expressly incorporated herein by reference thereto.

FIELD OF THE INVENTION

This invention relates to a bone screw, and, in particular, to a pedicle screw.

BACKGROUND OF THE INVENTION

Bone screws are typically used in internal fixation to anchor the fixation system to the relevant bone portions. For example, screws can be used in plate or rod systems to treat conditions such as vertebral instability. Overall these systems consist of a longitudinal support, i.e. the plate or rod, and anchoring elements, i.e. screws and/or hooks, for attaching the longitudinal support to the vertebrae. If screws are used, they usually pass through the pedicle and are accordingly referred to as pedicle screws. Because pedicle screws are stably affixed in the bone, they can provide more stability than hooks.

Regardless of the particular application, the design of the screw is very important since the design will have a direct impact on the short term and long term viability of the screw as a means for anchoring fixation systems to bone. In terms of design, the screw is broken up into two major sections, a head portion which, in the case of a pedicle screw, links to the fixation element, and a stem portion (or shaft) which anchors into the bone. The design of the shaft is particularly important in terms of short term and long term viability, with the short term stability dictated solely by mechanical considerations and the long term stability determined by a combination of mechanical (e.g. fatigue strength of the screw) and biological (e.g. bone/screw interface) considerations.

Pedicle screws in particular are subjected to bending and traction stresses. Excessive bending stress may result in "traumatically" or "biologically" cutting the pedicle screw in the bone and/or screw breakage. Pedicle screw rupture is a mechanical failure caused by fatigue while excessive traction only jeopardizes the bone-screw interface, not the screw itself.

The prior art teaches three basic types of three different thread designs. These are referred to throughout this specification as Types 1, 2, and 3, respectively, and are now summarized.

Type 1: Screws with Cylindrical Threads

The first type of screw is the cylindrical threaded screw. Both the body of the shaft and the threads of the screw are circular-cylindrical. This type of screw offers the highest resistance to extraction by tearing. Moreover, when the screw is rotated back (or backed out) over a distance of less than 10% of its length, the resistance to extraction by tearing is hardly effected. However, this screw design has several shortcomings relative to other designs:

Poor gripping of bone in the absence of careful predrilling;

Uncompensated widening of the entry site by the inward rotation of the screw, which results from lateral pressure exerted by soft tissue; and.

Wear on the thread in the bone during inward rotation (the longer the screw, the greater the wear).

Published European patent application 491,211 and U.S. Pat. No. 2,382,019 both disclose type 1 screws. The disclosed screws have two circular-cylindrical body segments of different body and outside diameters joined by a conical transition segment. The front part of the disclosed screws lack threading. Because of the absence of a thread on the front portion, the screw will provide poor gripping of the bone in the absence of large axial pressures. For brittle, sclerotic bones, the grip of the tip may be so poor that the bone thread will tear loose when attempting to drive the screw through the bone. Published European patent application 669,110 and U.S. Pat. No. 2,382,019 disclose a screw having a threaded front part, but the screw lacks a sequentially multi-stage configuration screw core.

Type 2: Screws With Fully Conical Threads

In these screws, both the body of the shaft and thread are conical. This type of screw offers the advantages of the ability to grip the bone tightly. However, this screw design has the drawback of having a sharp end that can cut into the comparatively soft, spongy, vertebral bone tissue. In addition, when this screw is rotated back, it does not retain the grip the bone as well, thereby increasing the tendency to loosen over time.

Type 3: Screws With Partly Conical Threads

This screw type has a conical body with a thread that is circular-cylindrical. Just as the type 1 screw, this screw is highly resistant to extraction by tearing on account of its cylindrical threads. However, there are several drawbacks to this screw design. First, if the screw is rotated back, the screw grip will likely loosen over time. In addition, although the danger for cutting is lower in this screw design in comparison to the conical screw, there still remains the possibility of cutting. Finally, as a result of the conical body shape and thread shape, the top of the screw shaft portion is wide which can result in bone fissures.

Thus, a need exists for an improved screw design that provides resistance to bending and cutting as well as improved resistance to extraction by tearing and offers good bone gripping independent of bone quality.

SUMMARY OF THE INVENTION

The present invention relates to a bone screw, and, in particular, to a pedicle screw. The screw has a head, a front portion having a thread and tapering convexly toward a tip, and a central portion. At least a section of the central portion has a contiguous thread with a substantially constant outside diameter. The threaded section comprises M segments having a body widening toward the head mutually alternating with N segments having a circular-cylindrical cross-section. M and N are integral numbers larger than 0 differing at most by a magnitude of 1, with M>1 and N>2.

In an exemplary embodiment, there are two N segments with the N segment nearer the head larger in diameter than the other N segment and the M segment tapers toward the front portion. The thread of the N segment nearer the head can be thicker than the thread of the other N segment.

The screw can include a non-threaded guide beak that is axially coupled to the tip of the front portion. The screw head can have a substantially frusto-spherical shape. Furthermore, a transition region can be located between the head and the central portion. This region can be threaded and preferably has a circular-cylindrical shape and a diameter that increases from the central portion toward the head. In one embodiment, the transition region thread has inner and outer diameters conically widening from the central portion toward the head. The transition region thread can have the same pitch as the threaded central portion section.

In one embodiment, the central portion section thread is a double thread, with a thread angle between 10° and 22° and a pitch between 3 and 5 mm. In another embodiment, the central portion section thread is a single thread, with a thread angle between 5° and 18° and a pitch between 1.5 and 4.0 mm. Regardless of the type of thread, the central portion section thread can be contiguous with the front portion thread. Additionally, the front portion thread and the central portion section thread can have the same pitch and comprise substantially similar number of thread turns.

In one embodiment, the convex taper runs tangentially into the central portion and has a cross sectional radius between 30 and 50 mm. In another embodiment, the front portion terminates in a spherical radius between 0.5 and 3.0 mm.

DETAILED DESCRIPTION OF THE PREFERRED EMBODIMENTS

The following description of the preferred embodiments of the present invention is merely exemplary in nature and is in no way intended to limit the subject invention or its application or uses.

Figures 1, 2:
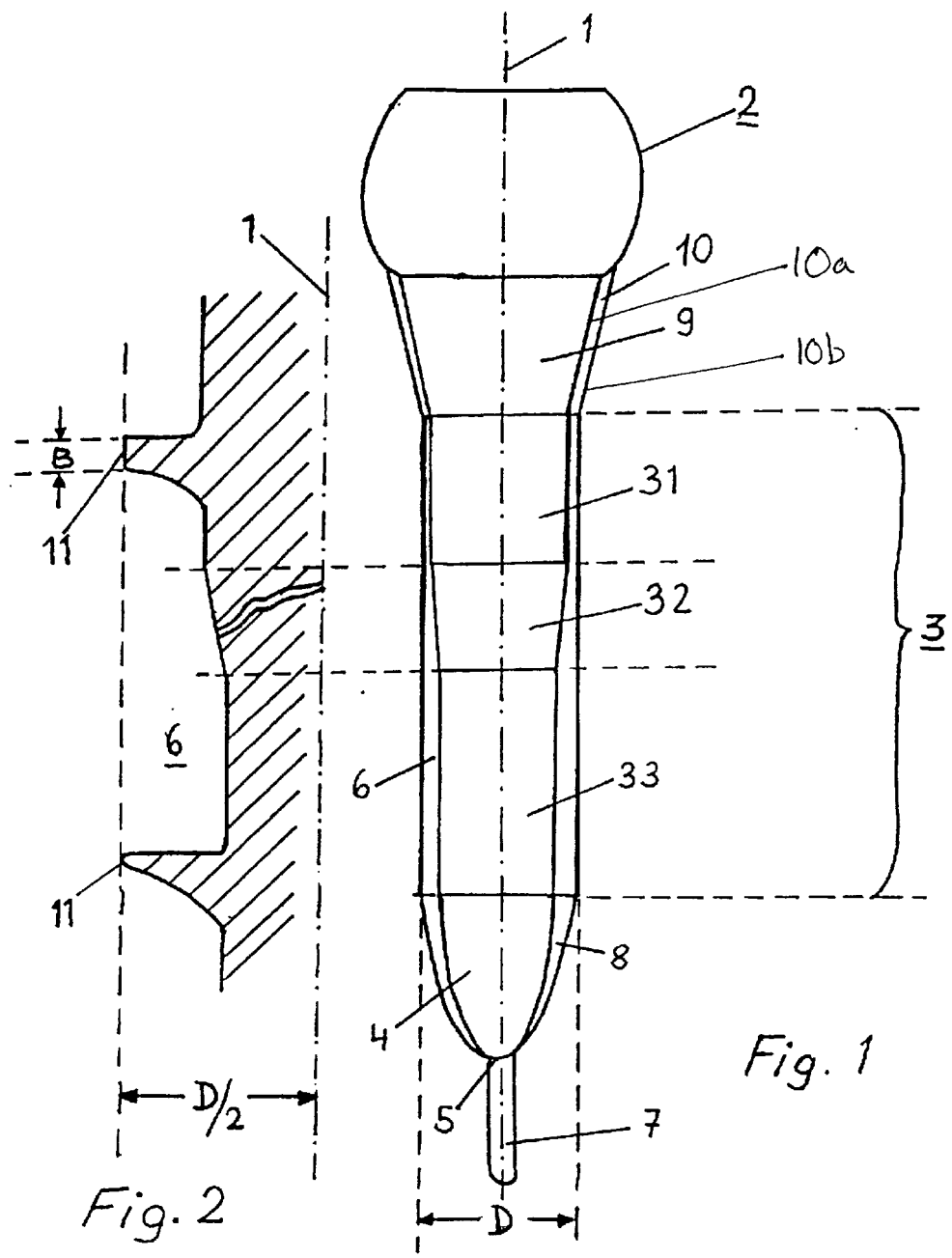
FIG. 1 shows a schematic of the cross-section of a screw according to the present invention.
FIG. 2 shows a detailed view of the threads taken from the central region of the screw.

Referring now to FIGS. 1 and 2, one embodiment of the screw according to the present invention is shown. The screw comprises a head 2, a central portion 3 having a thread 6, and a front portion 4 having tip 5. A central axis 1 is defined axially along central portion 3. In an exemplary embodiment, central portion 3 is made of three different segments 31, 32, and 33. Segment 33 is circular-cylindrical and is joined to front portion 4 and to segment 32. Segment 32 tapers conically in diameter at a half-cone angle, preferably, between 3° and 7° in the direction of tip 5 and joins segment 33 to segment 31. Segment 31 is circular-cylindrical and has a diameter larger than segment 33 and is joined to head 2 and segment 32. Preferably, segment 31 is 15% to 35% larger in diameter than segment 33. In addition, segment 33 itself may further comprise three segments (not shown) that are similarly shaped to segments 31, 32, and 33. In a preferred embodiment, central portion 3 is fitted with a continuous thread 6 and has a substantially uniform outside diameter of D.

As shown, front portion 4 tapers in the direction of tip 5 and is fitted with thread 8. The tip 5 includes a non-threaded circular-cylindrical guide beak 7 which runs axially to central axis 1.

Head 2 is frusto-spherical to allow using the screw in several axes. Head 2 is fitted with a recess, such as a hexagonal recess, to receive a mating protrusion in an insertion tool.

Transition region 9 increases in diameter from central portion 3 to head part 2. Alternatively, transition region 9 may be circular-cylindrical or circular-conical in shape. Preferably, transition region 9 is fitted with thread 10, which has an inner diameter 10a and an outer diameter 10b. The inner diameter 10a and/or the outer diameter 10b may expand conically from central portion 3 to head 2. Thread 10 and thread 6 can have match turn and the same pitch.

Typically, the pitch and the number of turns of threading on a screw will define the size of the gaps between the threads. These gaps essentially constitute a mechanically protected "rest zone" for the bone and optimizing these gap sizes results in improved biological anchoring.

Figure 3B:
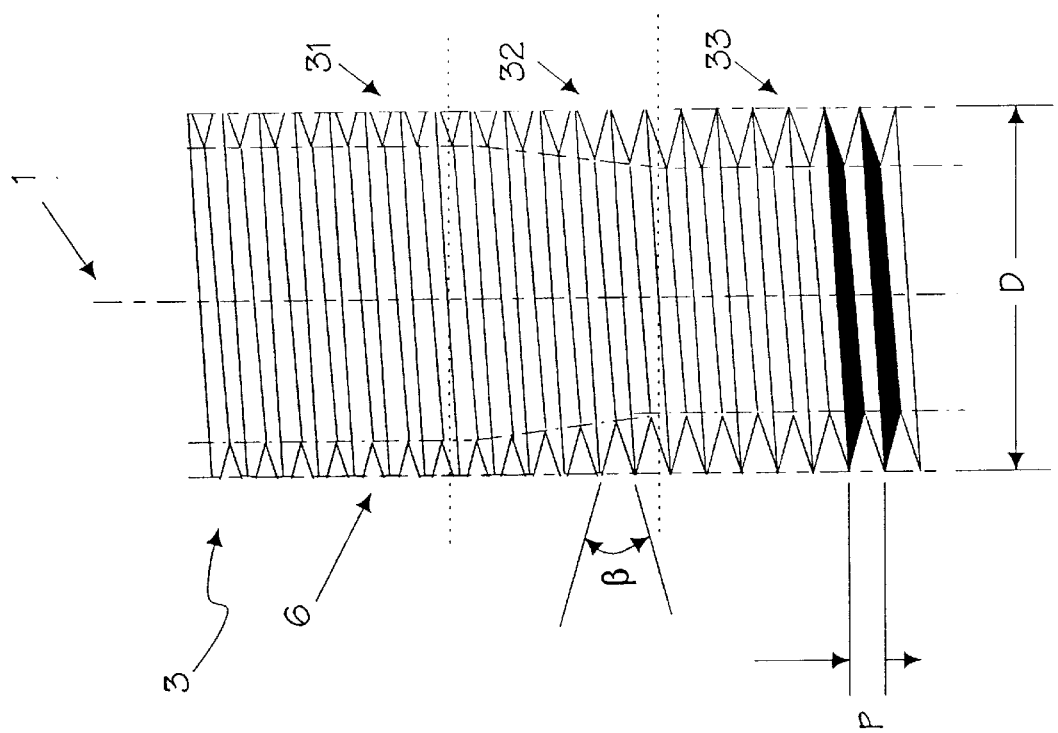
FIG. 3B shows an embodiment of the screw according to the present invention having a single thread on the central portion.
Figure 3A:
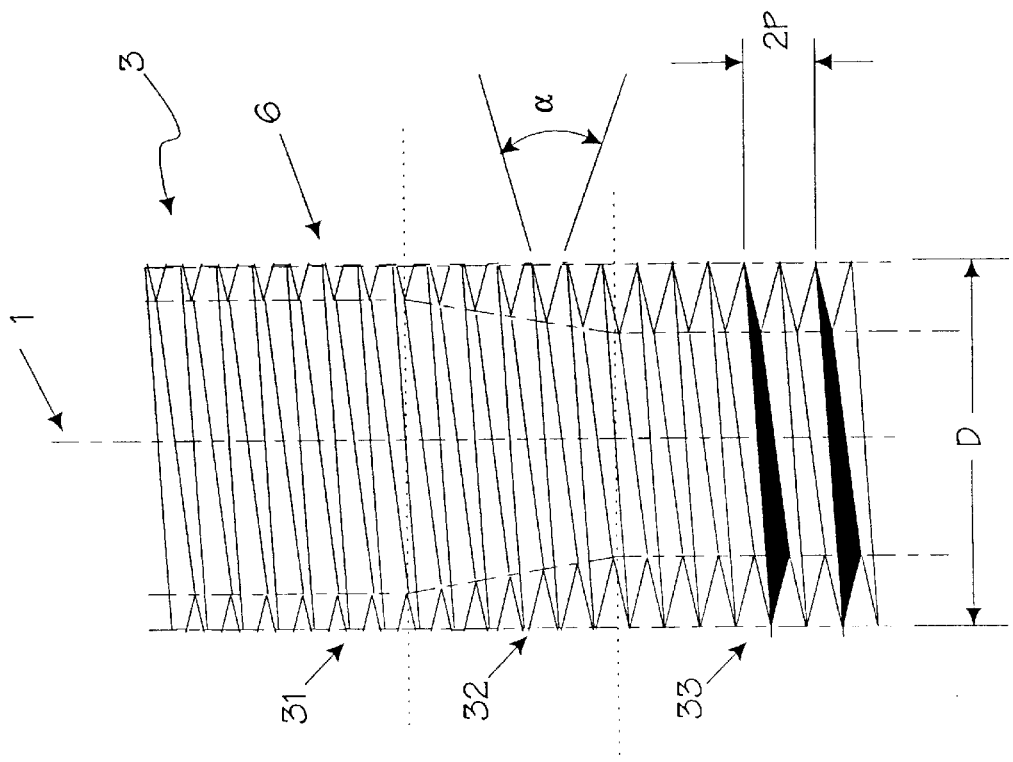
FIG. 3A shows an embodiment of the screw according to the present invention having a double thread on the central portion.

In one embodiment, shown in FIG. 3A, thread 6 of central portion 3 can be designed in the form of a double thread 2P having a thread angle $\alpha$ between 10° and 22°, but preferably between 14° and 18°. The pitch of thread 6 is between 3 and 5 mm, but preferably between 3.5 and 4.5 mm. In another embodiment, shown in FIG. 3B, thread 6 of central portion 3 is a single thread P. In this case the angle $\beta$ of thread 6 is between 5° and 18°, but preferably between 8° and 14°, and the pitch is between 1.5 mm and 4.0 mm, but preferably between 1.75 and 3.50 mm. In a preferred embodiment, the depth of thread 6 in the region of segment 31 is at least 0.2 mm but preferably is between 0.4 to 0.6 mm. In another preferred embodiment, the depth of thread 6 in the region of segment 31 is at least 0.5 mm, but preferably is between 0.6 to 1.0 mm. Thread 6 extends into front portion 4 of the screw stem. In a preferred embodiment, front portion 4 tapers toward tip 5 of the stem and is, preferably, convex conical in shape. The convex taper alternatively can run tangentially into the core of central portion 3 with a cross sectional radius between 30 and 50 mm and can be cross-sectionally parabolic.

Thread 8 of front portion 4 and thread 6 of central portion 3 are, in one embodiment, of the same pitch and have the same number of threads. Thread 6 of central portion 3 merges continuously with thread 8 of front portion 4 and thread 8 tapers in a convex, parabolic, or conical manner toward tip 5. Cross-sectionally, the radius of the taper of thread 8 is between 20 and 40 mm. It may also be parabolic. Front portion 4 can terminate in a spherical radius between 0.5 and 3.0 mm, preferably between 1.5 and 2.0 mm.

FIG. 2 shows a detailed view of the threading on the stem portion of the screw. In one embodiment, thread tops 11 of thread 6 are thicker in the region of segment 31 than in the region of segment 33. The difference between the diameter of segment 33 and segment 31 is selected, preferably, so the tops 11 of thread 6 in the area of segment 31 are of a width B which is between 0.3 and 0.5 mm.

The screw according to the present invention provides many advantages over the prior art. Some of these advantages are now listed with specific reference to the feature(s) of the screw are primarily responsible for the improved characteristics. For example, the screw's threaded stem has a constant outside diameter, which results in optimal resistance to extraction by tearing and is especially clinically significant during use as a pedicle screw. The tapering end portion and guide beak allows the screw to grip the bone without any need for additional axial pressure and reduces the danger of fissuring or extraction by tearing. The tapered end and guide beak also allows the screw to be guided and centered easily thereby minimizing the danger of lateral penetration of bone by the screw.

In another embodiment, the body of the screw stem has a narrow diameter section and a larger diameter section with a conically tapering linking section. This embodiment has several advantages over the prior art. First, the widening of the entry site caused by rotation of the screw is compensated by the section of the screw stem with the larger body diameter. Second, the resistance to extraction by tearing and cutting of the screw within the bone is significantly independent of the screw being rotated back. Third, optimal cutting resistance of the screw in the bone results from strong anchoring in the vicinity of the screw tip and in the vicinity of entry site.

In another embodiment, the thickness of the threads is constant over the length of the shaft and the thickness of the outermost edge of the threads depends on the diameter of the body of the stem. The larger body segment has the thicker outermost thread edges while the thinner body segments will have the thinner outermost thread edges. This variance in the body diameter of the stem with a constant outside diameter allows for the wedging efficacy of the screw to be optimized.

In a further embodiment, the tapering end portion of the stem is linear-conical or convex. This design offers the advantage of improved centering and guiding of the screw and optimizing thread gripping while minimizing bone fissuring. The threading on the stem of the screw can be double-threading, which provides improved hole centering, quicker implantation time, and an improved grip and bracing in the bone.

To better explain the advantages of the screw of the present invention, the use of the screw as a pedicle screw will now be described. Initially, the pedicle is opening using an awl, drill, or similar tool. The hole that is created has a diameter that is smaller than the smallest diameter of the screw, i.e. segment 33. The screw will then be introduced to the borehole and rotated in a direction of inward progression. When the screw is rotated, front portion 4 with thread 8 widens the borehole in the spongeous bone with minimal fissuring. The displaced spongeous bone is compressed in the region of thread 6.

Frequently, the soft tissue hampers rotating of the screw. The lateral pressure from the soft tissue may, upon initial rotation, entail insertion of the screw in a "wobbly" manner and widening of the hole near the entry site. However, the screw will increasingly stabilize with increasing depth of penetration.

Segments 31 and 33 are matched to each other so that segment 31 will only penetrate the bone after the screw has been stabilized. This is accomplished by segment 32 which widens the inside diameter of the borehole via its conical shape so when segment 31 enters the borehole, the diameter of the borehole is matched to the diameter of segment 31 and by the thickness of thread tops 11 which increase in width uniformly as the diameter of the body of the stem increases. Also, the lengths of stem segments 9, 31, 32, 33, and 8 are sized so there will be optimal gripping of the surrounding bone by the screw. Finally, to minimize fissuring, the diameters of the segments in the screw stem are matched to each other so that the thickness of thread tops 11 is between 0.2 and 0.5 mm.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A bone screw having a central axis and including a head, a front portion having a thread and tapering toward a tip, and a central portion, wherein at least a section of the central portion comprises:

a contiguous thread with a substantially constant throughout said at least a section of the central portion outside diameter; and M segments having a body widening toward the head and N segments having a circular-cylindrical cross-section, wherein $M \geq 1$ and $N \geq 2$, with M and N integral numbers larger than 0 and differing at most by a magnitude of 1, and the M and N segments mutually alternate.

2. The screw of claim 1 further comprising a non-threaded guide beak that is axially coupled to the tip of the front portion.

3. The screw of claim 1 wherein the screw head has a substantially frusto-spherical shape.

4. The screw of claim 1 further comprising a transition region located between the head and the central portion and having a circular-cylindrical shape.

5. The screw of claim 4 wherein the transition region has a diameter that increases from the central portion toward the head.

6. The screw of claim 4 wherein the transition region has a thread.

7. The screw of claim 6 wherein the transition region thread has inner and outer diameters conically widening from the central portion toward the head.

8. The screw of claim 6 wherein the transition region thread and the thread on the section of the central portion have the same pitch.

9. The screw of claim 1 wherein the thread on the section of the central portion is a double thread.

10. The screw of claim 9 wherein the thread on the section of the central portion has a thread angle between 10° and 22°.

11. The screw of claim 9 wherein the thread on the section of the central portion has a pitch between 3 and 5 mm.

12. The screw of claim 1 wherein the thread on the section of the central portion is a single thread.

13. The screw of claim 12 wherein the thread on the section of the central portion has a thread angle between 5° and 18°.

14. The screw of claim 12 wherein the thread on the section of the central portion has a pitch between 1.5 and 4.0 mm.

15. The screw of claim 1 wherein the thread on the section of the central portion is contiguous with the front portion thread.

16. The screw of claim 1 wherein the front portion is convexly tapered toward the tip, and the convex taper runs tangentially into the central portion and has a cross sectional radius between 30 and 50 mm.

17. The screw of claim 1 wherein the front portion thread and the thread on the section of the central portion have the same pitch and comprise substantially similar number of thread turns.

18. The screw of claim 1 wherein the front portion terminates in a spherical radius between 0.5 and 3.0 mm.

19. The screw of claim 1 wherein there are two N segments with the N segment nearer the head larger in diameter than the other N segment and the M segment tapers toward the front portion.

20. The screw of claim 19 wherein the N segment nearer the head has a thread that is thicker than a thread located on the other N segment.

21. A bone screw comprising:

a screw head;

a front portion tapering towards a tip; and a central portion disposed between the head and the front portion, at least a section of the central portion including a substantially contiguous thread defining a thread inner diameter and a thread outer diameter;

wherein the thread outer diameter is substantially constant, and the thread inner diameter varies along the at least a section the central portion.

22. The bone screw of claim 21, wherein the at least a section of the central portion includes at least one segment along which the thread inner diameter increases toward the screw head.

23. The bone screw of claim 22, wherein the section of the central portion includes at least one segment along which the thread inner diameter defines a substantially frusto-conical shape.

24. The bone screw of claim 22, wherein the at least a section of the central portion includes at least one segment along which the thread inner diameter defines a substantially circular-cylindrical shape.

25. The bone screw of claim 21, wherein the at least a section of the central portion defines a first longitudinal end and a second longitudinal end, and includes a first segment substantially adjacent the first longitudinal end, a second segment substantially adjacent the second longitudinal end, and a third segment substantially intermediate the first and second segments, wherein the thread inner diameter is substantially constant along the first and second segments, and the thread inner diameter increases toward the screw head along the third segment.

26. The bone screw of claim 25, wherein the thread inner diameter is larger at the first segment than at the second segment.

27. The bone screw of claim 25, wherein the thread inner diameter defines a substantially circular-cylindrical shape along the first and second segments, and the thread inner diameter defines a substantially frusto-conical shape along the third segment.

28. The bone screw of claim 21, wherein the screw head has a substantially frusto-spherical shape.

29. The bone screw of claim 21, further comprising a non-threaded guide beak connected to the tip.

30. The bone screw of claim 21, further comprising a transition region located between the screw head and the central portion, wherein the transition region has a diameter that increases from the central portion toward the screw head.

31. A bone screw comprising:

a screw head having a substantially frusto-spherical shape;

a front portion tapering toward a tip; and a central portion disposed between the head and the front portion, wherein at least a section of the central portion includes a substantially contiguous thread defining a thread inner diameter and a thread outer diameter, and the thread inner diameter varies along the at least a section, and wherein the thread outer diameter is substantially constant along the at least a section of the central portion.

32. The bone screw of claim 31, wherein the at least a section of the central portion includes at least one segment along which the thread inner diameter defines a substantially frusto-conical shape.

33. The bone screw of claim 32, wherein the at least a section of the central portion includes at least one segment along which the thread inner diameter defines a substantially circular-cylindrical shape.

34. The bone screw of claim 31, wherein the at least a section of the central portion defines a first longitudinal end and a second longitudinal end, and includes a first segment substantially adjacent the first longitudinal end, a second segment substantially adjacent the second longitudinal end, and a third segment substantially intermediate the first and second segments, wherein the thread inner diameter is substantially constant along the first and second segments, and the thread inner diameter increases toward the screw head along the third segment.

* * * * *